United States Patent [19]
Martin

[11] Patent Number: 5,417,660
[45] Date of Patent: May 23, 1995

[54] SELF-LOCKING SYRINGE HOLDER FOR USE WITH A HYPODERMIC SYRINGE

[75] Inventor: Robin P. Martin, Lufkin, Tex.

[73] Assignee: T. A. Kershenstine, Kenner, La.

[21] Appl. No.: 198,408

[22] Filed: Feb. 22, 1994

Related U.S. Application Data

[63] Continuation-in-part of Ser. No. 46,039, Apr. 12, 1993, Pat. No. 5,318,538, which is a continuation-in-part of Ser. No. 870,641, Apr. 16, 1992, Pat. No. 5,242,420, which is a continuation-in-part of Ser. No. 829,708, Feb. 3, 1992, Pat. No. 5,201,708.

[51] Int. Cl.⁶ ............................................. A61M 5/00
[52] U.S. Cl. .................................... 604/110; 604/198; 604/263
[58] Field of Search ............... 604/110, 198, 263, 192, 604/187

[56] References Cited

U.S. PATENT DOCUMENTS

| 5,282,793 | 2/1994 | Larson | 604/198 X |
| 5,300,038 | 4/1994 | Haber et al. | 604/198 X |

*Primary Examiner*—John D. Yasko
*Attorney, Agent, or Firm*—Keaty & Keaty

[57] ABSTRACT

The invention relates to a self-locking syringe holder adapted for use with conventional hypodermic syringes and designed to prevent accidental puncturing of the medical attendant by an infected syringe needle. The holder has a hollow casing which receives the syringe barrel therein and which is provided with a pair of grooves within which locking tabs of a needle guard can move. Mounted within the casing is a compressible tension spring which continuously urges the needle guard into a fully extended position. To prevent misalignment of a needle guard with the casing, the needle guard is formed with a pair of longitudinal projections extending outwardly from an exterior surface of the needle guard and engageable with their respective cut-out grooves formed in an end plate of a proximal end of the casing.

16 Claims, 3 Drawing Sheets

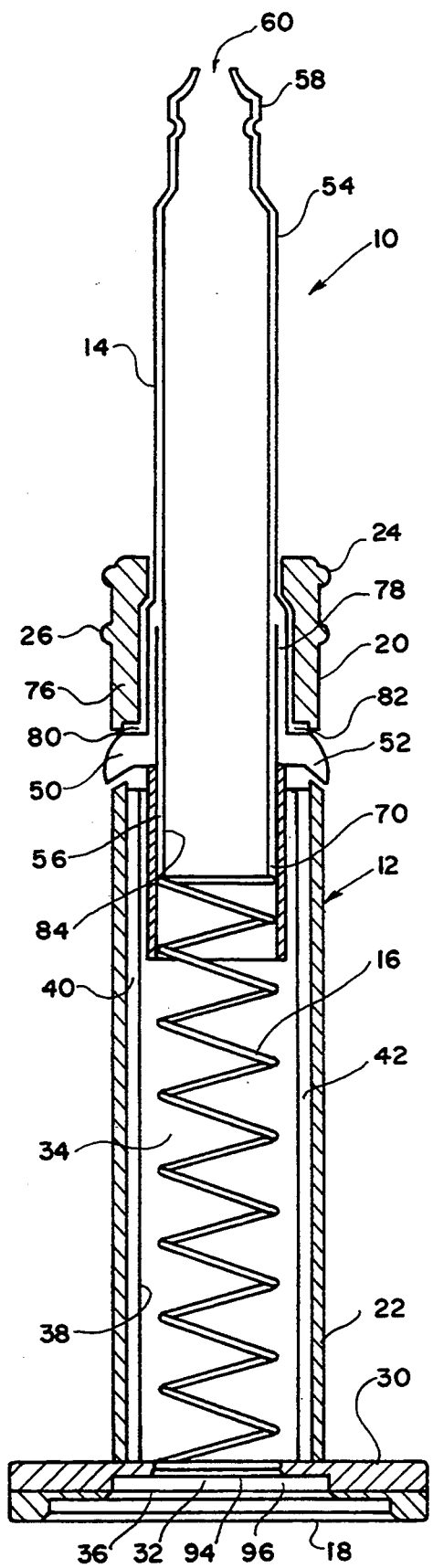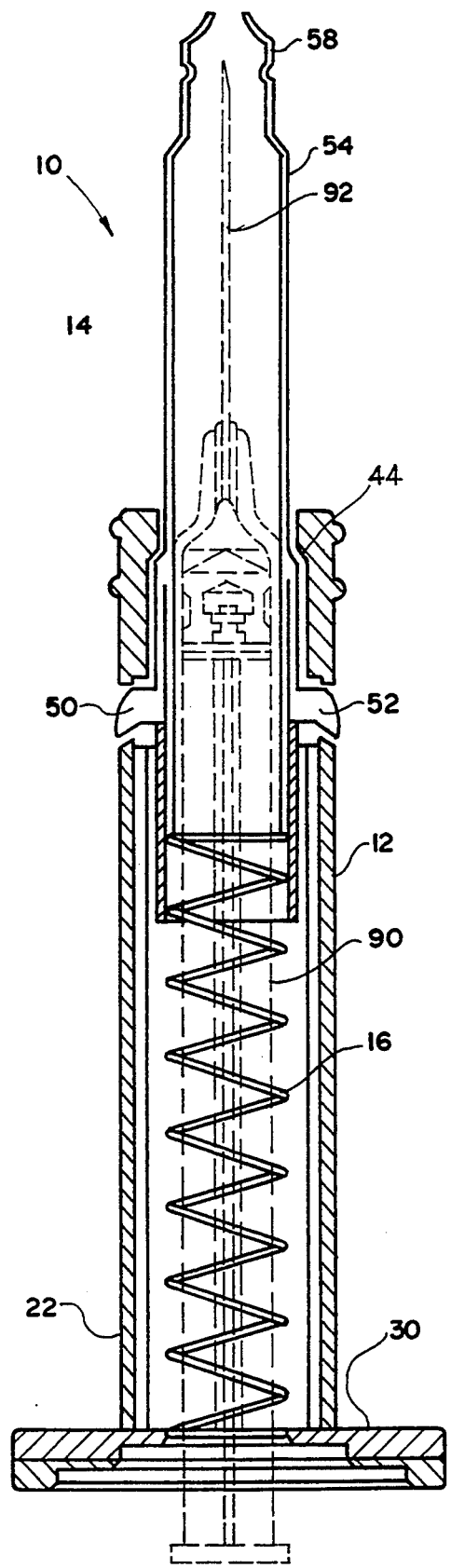
F I G. 1
F I G. 2

SELF-LOCKING SYRINGE HOLDER FOR USE WITH A HYPODERMIC SYRINGE

CROSS-REFERENCE TO RELATED APPLICATIONS

This is a continuation-in-part of my application Ser. No. 046,039 filed on Apr. 12 1993, entitled "self-Locking Safety Syringe"; now U.S. Pat. No. 5,318,538, which is a continuation-in-part of U.S. Pat. No. 5,242,420, Ser. No. 870,641, filed on Apr. 16, 1992, entitled "Self-Locking Safety Syringe", which is a continuation-in-part of U.S. Pat. No. 5,201,708, Ser. No. 829,708, filed on Feb. 3, 1992, entitled "Self-Locking Safety Syringe", the full disclosures of which are incorporated by reference herein.

BACKGROUND OF THE INVENTION

This invention relates to medical equipment, and more particularly to a safety device for use with conventional hypodermic syringes designed to prevent accidental needle stick injuries by medical personnel, before, after, or during administration of an injection.

The ever increasing spread of diseases transmitted by blood and other bodily fluids, such as the Acquired Immune Deficiency Syndrome and Hepatitis B, creates a real threat to medical personnel of accidental, inadvertent puncturing of the skin by a syringe needle, which has been in contact with an infected patient, and of the transmittal of the often fatal disease to the unfortunate medical attendant. Despite educational programs carried by many hospitals, accidents continue to happen with an unfortunate effect on medical personnel being infected through coming in contact with bodily fluids of a patient.

Numerous attempts have been made to resolve this problem by proposing to use a protective syringe needle guard which would cover the needle when it is not in use, and thereby prevent the needle from being exposed during the time of injection or immediately following the injection. However, such devices are expensive to manufacture and difficult to use, requiring several steps in preparation of the syringe for utilization and, so far, have not found wide acceptance in the medical profession.

The present invention contemplates the elimination of drawbacks associated with the prior art and provision of an improved syringe holder, which is particularly adapted to prevent exposure of the needle outside of the holder at all times.

SUMMARY OF THE INVENTION

It is, therefore, a general object of the present invention to provide a self-locking safety syringe holder which is designed to prevent accidental exposure of the needle.

It is another object of the present invention to provide a syringe holder which covers the needle at all times during manipulation of the syringe.

It is a further object of the present invention to provide a syringe holder which is easy to use and inexpensive to manufacture.

These and other objects of the present invention are achieved through a provision of an elongated tubular hollow casing which is provided with a pair of diametrically opposite inner grooves formed in the annular interior wall thereof. An elongated hollow needle guard telescopically co-axially engages with the casing, with a portion of the needle guard carrying a pair of locking tabs, each mounted on a respective resilient support. The supports force the locking tabs outwardly through apertures formed in the body of the casing to lock the needle guard with the casing. To prevent misalignment of the needle guard and the casing, the needle guard carries a pair of diametrically opposite projections extending longitudinally along a middle portion of the needle guard and engageable within respective cutout grooves formed in an end plate of a proximal end of the casing. The end plate restricts the opening formed in the proximal end. The grooves frictionally engage the projections when the needle guard is forced telescopically into the casing.

A plurality of circumferentially spaced ridges formed at a proximal end of the casing form an abutting surface for the needle guard, when the needle guard is positioned within the casing to prevent the needle guard from exiting from the proximal end of the casing when installed telescopically within the casing.

A plurality of elongated projections are formed on an interior surface of the inner portion of the needle guard. These projections serve as an abutting surface against which a compressible resilient tension spring means urges. The second end of the spring means urges against a flange plate of the syringe when the holder is assembled with the syringe. To ensure containment of the spring means and hypodermic syringe in a fixed position during use, a cap is provided at the distal end of the casing. The cap snaps with a flange plate of the casing and closes the opening in the casing.

BRIEF DESCRIPTION OF THE DRAWINGS

Reference will now be made to the drawings, wherein like parts are designated by like numerals, and wherein:

FIG. 1 is a cross sectional view of the device in accordance with the present invention.

FIG. 2 is a view of the holder in conjunction with a hypodermic needle (shown in phantom lines), with the needle guard in a fully extended position.

DETAILED DESCRIPTION OF THE PREFERRED EMBODIMENT

Figure 3:
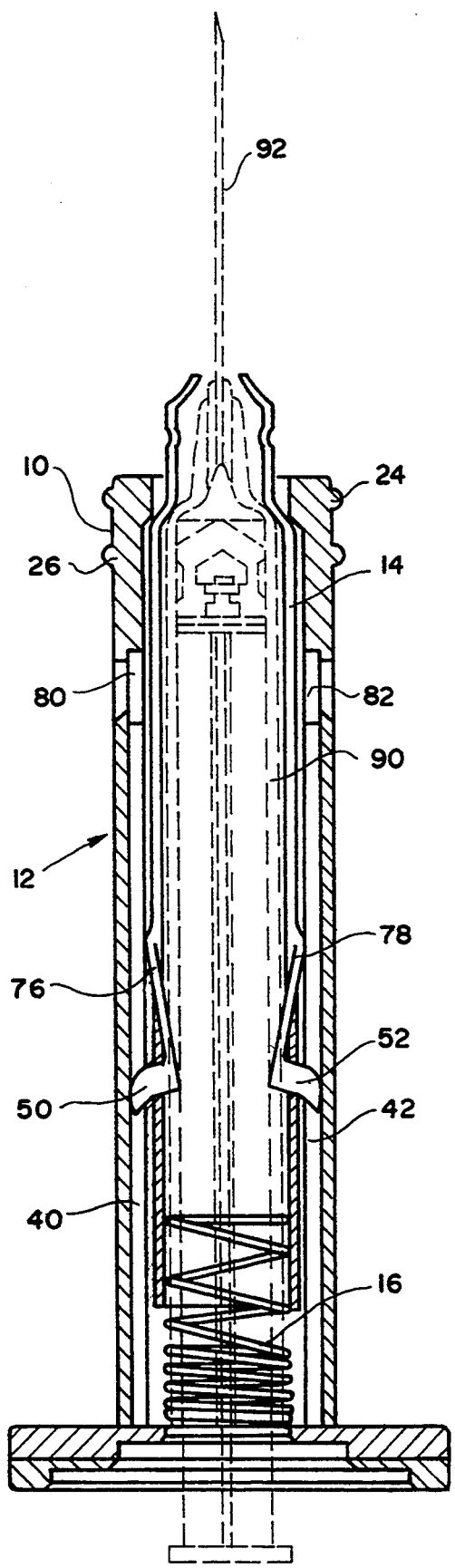
FIG. 3 is a view of the device in accordance with the present invention in use with a hypodermic needle, with the needle guard in a retracted position.
Figure 4:
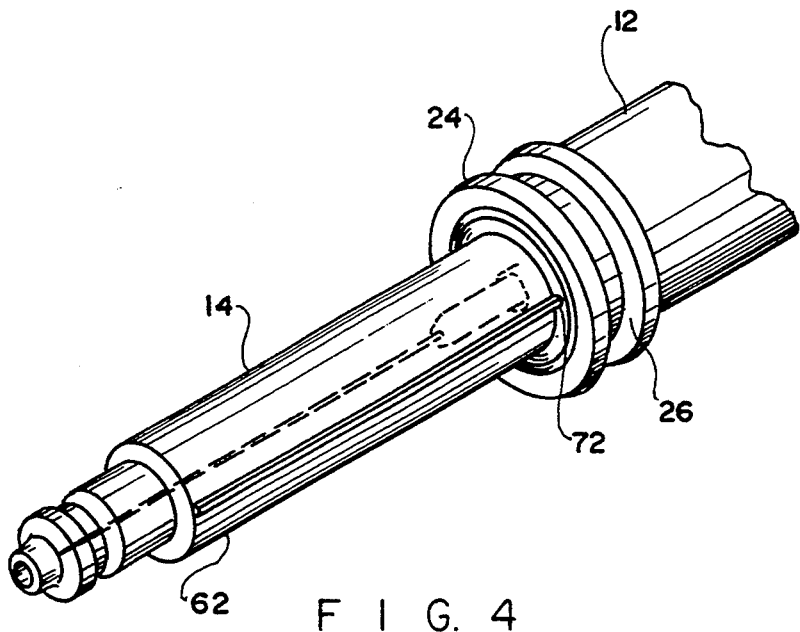
FIG. 4 is a detail view showing proximal ends of a casing and a needle guard.
Figure 5:
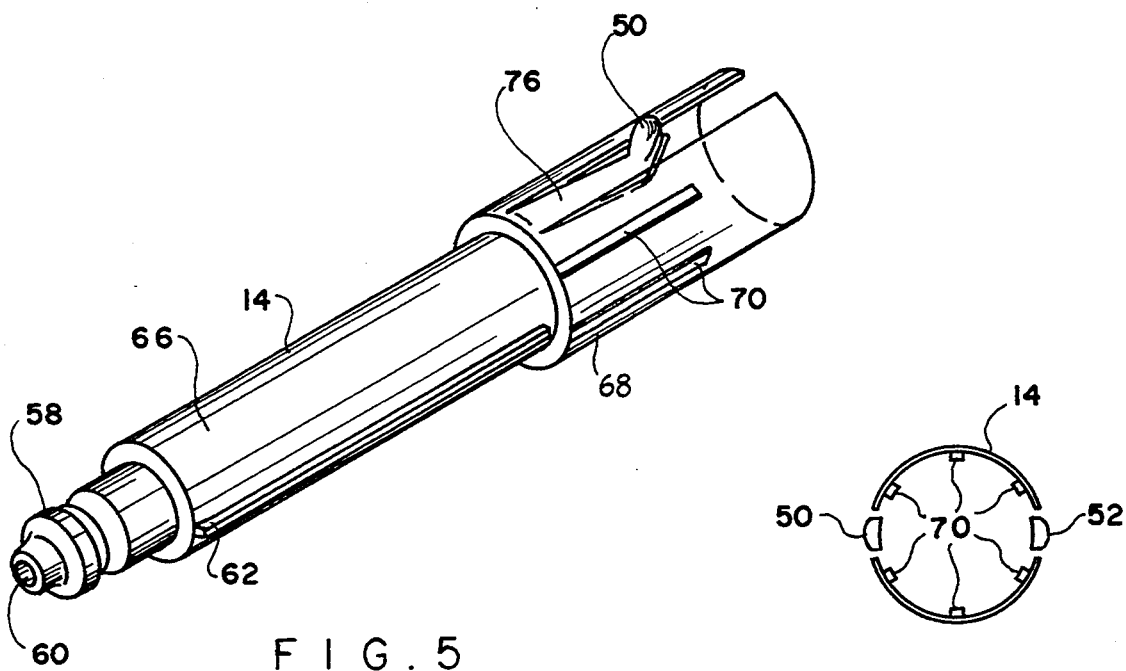
FIG. 5 is a detail view showing the needle guard.
Figure 6:
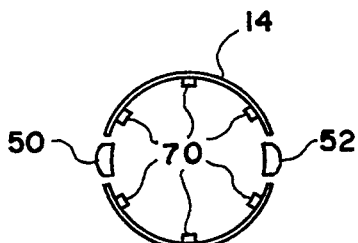
FIG. 6 is an end view of the needle guard.

Referring now to the drawings in more detail, numeral 10 designates the syringe holder in accordance with the present invention. The holder device comprises a casing 12, a needle guard 14, compressible tension spring means 16 and a cap 18. The casing 12 is a lightweight hollow, generally cylindrical body having a proximal end 20 and a distal end 22. The proximal end 20 is provided with a pair of spaced-apart annular ribs 24 and 26 which are integrally formed with the body of the casing 12 and are designed to assist the user in holding the device 10 by increasing friction of the user's fingers on the casing.

The distal end 22 of the casing 12 is provided with an irregularly shaped flange 30 which extends outwardly from the edge of the casing 12 transversely to a longitudinal axis thereof. An irregularly shaped groove 32 is formed on the exterior surface of the flange 30, with the groove 32 being greater in dimension then the central opening 34 extending through the length of the casing 12. The groove 32 is adapted to receive an inner surface of a syringe flange 36 when the syringe is assembled with the holder 10.

The central opening 34 of the casing 12 is defined by an annular wall 38 which is made preferably smooth and protrusion-free. A pair of elongated grooves 40 and 42 are formed diametrically opposite each other in the annular wall 38 to allow locking tabs 50 and 52, respectively, of the needle guard 14 to slide therein, when the needle guard 14 is moved into its retracted position(s).

The needle guard 14, similarly to the casing 12, is made substantially hollow and has a generally cylindrical configuration. The exterior of the needle guard 14 is slightly smaller than the inner diameter of the central opening 34, so as to allow the needle guard 14 to telescopically move within the casing 12 between a plurality of successively retracted positions and a fully extended position.

The needle guard 14 has a proximal end 54 and a distal end 56. Formed at the proximal end 54 is a reduced diameter nose portion 58 which has an opening 60 wide enough to allow a needle to pass therethrough, while not wide enough to allow the needle assembly hub to pass through. The needle guard 14 is provided with a pair of alignment ridges 62 and 64 formed on the exterior of the needle guard and extending through substantially entire portion 66 of the needle guard.

The ridges 62 and 64 extend in parallel relationship to the longitudinal axis of the needle guard and are slidably received within respective cutouts 72 and 74 made in the proximal end 20 of the casing 12. The cutouts 72 and 74 are made just wide enough to allow sliding of the ridges 62 and 64, respectively, and deep enough to receive the entire thickness of the ridges therein. In this manner, the ridges 62 and 64 are frictionally fitted within the cutouts 72 and 74. The needle guard 14 is thereby prevented from rotation in relation to the casing 12, and is always kept in a preselected alignment with the casing 12.

The distal portion 56 of the needle guard 14 is provided with a pair of locking tabs 50 and 52. The tabs 50 and 52 are each carried by a respective resilient depressible support 76 and 78. When in a locked position, the locking tabs 50 and 52 extend through corresponding apertures 80 and 82 made in the casing 12 adjacent to the proximal end 20 of the casing.

When in a locked position, the needle guard 14 is prevented from retracting inwardly into the casing 12 by the tabs 50 and 52 which are forced out through the apertures 80 and 82 by a resilient force of their respective supports 76 and 78. However, once manually depressed, the locking tabs 50 and 52 move inwardly through the apertures 80 and 82 into the respective grooves 40 and 42 and are allowed to slide therein as long as a compressive force is applied to the nose portion 58 of the needle guard 14.

The inner portion 68 of the needle guard 14 is further provided with a plurality of inwardly extending ridges 70 which are formed on the inner annular wall 84, so as to form a stop and abutting surface for the compressible tension spring 16 mounted within the casing 12 and extending in a surrounding relationship about at least a portion of the syringe barrel 90. As can be seen in the drawings, the syringe is positioned inside the casing and the needle guard in such a manner, that the needle 92 is located in a co-axial alignment with the central axis of the casing 12 and the needle guard 14. The syringe barrel 90 fits within the longitudinal dimensions of the casing 12 and needle guard 14 and is attached by the syringe barrel flange 96 at the distal end of the casing flange 30.

The needle guard 14 fits within the longitudinal dimensions of the casing 12, and is prevented from sliding out of the casing 12 by a plurality of stops 44 of the casing 12 adjacent to the proximal end 20. When in an assembled position, the outer surface of the needle guard 14 abuts the stops 44, while the flange of the syringe barrel is fitted within the groove 32 of the casing flange 30.

The inner surface 94 of the syringe flange 96 serves as an abutting surface for the second end of the tension spring 16 when the syringe is assembled with the holder 10. To prevent the spring 16 from falling out of the casing 12, the cap 18 closes the opening 34 at the distal end 22 of the casing 12 by "snapping" with the flange 30 prior to the use of the syringe holding device.

When the syringe is ready to be positioned within the holder 10, the cap 18 is removed, and the syringe barrel 90 with plunger is placed within the casing 12 in such a manner, that the spring 16 surrounds the syringe barrel, while the needle 92 extends into the needle guard 14 towards the nose portion 58. At that time the locking tabs 50 and 52 are in their extended position and the needle guard 14 is in its fully extended position, as well. Once the syringe is placed in the holder 10, the cap 18 is again replaced in a frictionally fixed engagement with flange 30, with the cap 18 retaining the syringe and spring in place.

During use, the locking tabs 50 and 52 are depressed and the nose portion is placed against a stopper of a medication vial. A slight compressive force is applied to the needle guard 14 by forcing the casing 12 towards the vial. This force is sufficient to move the needle guard 14 some distance inside the casing 12 and allowing the tip of the needle to penetrate the stopper of the vial to extract the medicine.

Once the medicine is withdrawn, the locking tabs are released, and the casing 12 is pulled outwardly from the vial. This action causes the needle guard to be forced forward by the tension spring 16 and cover the needle 92 as soon as it leaves the vial. An injection is performed in a similar manner, with the needle guard 14 covering the entire needle 92 at all times, except for that portion of the needle 92 which is forced into the body of the patient for performing the injection.

The holder 10 provides an inexpensive and easy solution to the problem of accidental needle pricking by the medical personnel and protects the attendant from infection by the bodily fluid of a patient. It is envisioned that the casing and the needle guard can be made of lightweight material, such as plastic, while the tension spring 16 can be made from a steel wire or similar material. If desired, the holder can be made transparent with indicia imprinted thereon corresponding to the volume contents of a conventional syringe. As will be appreciated, the holder 10 can be made of various sizes to accommodate different size syringes, length of the needle, etc.

In an alternative embodiment, the needle guard can be made along with the casing to have just one locking tab.

Many changes and modifications can be made within the design of the present invention without departing from the spirit thereof. I, therefore, pray that my rights to the present invention be limited only by the scope of the appended claims.

I claim:

1. A self-locking safety holder for a hypodermic syringe having a syringe barrel and a needle assembly, the holder comprising:
   an elongated hollow tubular casing;
   an elongated hollow tubular needle guard telescopically co-axially engaged with the casing, with at least a portion of said needle guard extending outwardly from a forward end of said casing, the needle guard being movable between a first position in locking engagement with the casing and a plurality of retracted positions;
   a resilient depressible means for locking the needle guard in the first position, said locking means being carried by an exterior of the needle guard; and
   a resilient elastic means for continuously urging the needle guard into the first position to thereby prevent accidental movement of the needle guard from the locked position even after the locking means have been depressed, said elastic means being mounted within a central opening formed in the casing.

2. A self-locking safety holder for a hypodermic syringe having a syringe barrel and a needle assembly, the holder comprising:
   an elongated hollow tubular casing;
   an elongated hollow tubular needle guard telescopically coaxially engaged with the casing, the needle guard being movable between a first position in locking engagement with the casing and a plurality of retracting positions, wherein said needle guard has a narrow nose portion, a middle portion and an inner portion, and wherein said inner portion is provided with a plurality of ridges extending inwardly from an annular inner wall of the needle guard in a substantially parallel relationship to a longitudinal axis of the needle guard
   a resilient depressible means for locking the needle guard; in the first position, said locking means being carried by exterior of the needle guard; and
   a resilient elastic means for continuously urging the needle guard into the first position to thereby prevent accidental movement of the needle guard from the locked position even after the locking means had been depressed, said elastic means being mounted in a central opening formed in the casing.

3. The device of claim 2, wherein said elastic means comprises a coil spring having a first end, which urges against said inner portion ridges, and a second end, which urges against a flange plate of the syringe barrel, when the holder and the 4. The device of claim 1, wherein said locking means comprises at least one locking tab mounted on a resilient support secured to the needle guard, said resilient support continuously urging the locking tab into a locked position with the casing.

5. A self-locking safety holder for hypodermic syringe having a syringe barrel and a needle assembly, the holder comprising:
   an elongated tubular casing;
   an elongated hollow tubular needle guard telescopically coaxially engaged with the casing, the needle guard being movable between a first position in locking engagement with the casing and a plurality of retracted positions;
   a resilient depressible means for locking the needle guard in the first position, said locking means being carried by an exterior of the needle guard, said locking means comprising at least one locking tab mounted on a resilient support secured to the needle guard, said resilient support continuously urging said at least one locking tab into a locked position with the casing, wherein at least one aperture is formed in the casing to allow the locking tab to extend therethrough when the tab is in a locked position, while permitting manual depression of the locking tab against the outwardly directing force exerted by the supporting member; and
   a resilient elastic means for continuously urging the needle guard into the first position to thereby prevent accidental movement of the needle guard from the locked position even after the locking means have been depressed, said elastic means being mounted within a central opening formed in the casing. syringe are assembled together.

6. The device of claim 5, wherein at least one longitudinal groove is formed in an inner annular wall of the casing to allow the locking tab to slide therein, after the locking tab has been depressed.

7. The device of claim 1, wherein said holder is further provided with means to prevent misalignment of the needle guard in relation to the casing.

8. A self-locking safety holder for a hypodermic syringe having a syringe barrel and a needle assembly, the holder comprising:
   an elongated hollow tubular casing;
   an elongated hollow tubular needle guard telescopically co-axially engaged with the casing, the needle guard being movable between a first position in locking engagement with the casing and a plurality of retracted positions;
   a resilient depressible means for locking the needle guard in the first position, said locking means being carried by an exterior of the needle guard; and
   a resilient elastic means for continuously urging the needle guard into the first position to thereby prevent accidental movement of the needle guard from the locked position even after the locking means have been depressed, said elastic means being mounted within a central opening formed in the casing, wherein said holder is provided with means to prevent misalignment of the needle guard in relation to the casing, wherein said means for preventing misalignment comprise at least one elongated projection formed on an exterior surface of the needle guard, said at least one projection being engageable with a groove formed in a proximal end of the casing.

9. A self-locking safety holder for a hypodermic syringe having a syringe barrel and a needle assembly, the holder comprising:
   an elongated hollow tubular casing;
   an exterior surface of said casing being provided with a pair of annular ribs to facilitate secure manual engagement of the casing by a user;
   an elongated hollow tubular needle guard telescopically co-axially engaged with the casing, the needle guard being movable between a first position in locking engagement with the casing and a plurality of retracted positions;
   a resilient depressible means for locking the needle guard in the first position, said locking means being carried by an exterior of the needle guard; and a resilient elastic means for continuously urging the needle guard into the first position to thereby prevent accidental movement of the needle guard from the locked position even after the locking means have been depressed, said elastic means being mounted within a central opening formed in the casing.

10. A self-locking safety holder for a hypodermic syringe having a syringe barrel and a needle assembly, the holder comprising:

an elongated hollow tubular casing;

an elongated hollow tubular needle guard telescopically co-axially engaged with the casing, the needle guard being movable between a first position in locking engagement with the casing and a plurality of retracted positions, wherein a plurality of circumferentially spaced inner stops are formed on the interior surface of the casing adjacent its proximal end, said stops forming an abutting surface for a forward end of the needle guard;

a resilient depressible means for locking the needle guard in the first position, said locking means being carried by an exterior of the needle guard; and a resilient elastic means for continuously urging the needle guard into the first position to thereby prevent accidental movement of the needle guard from the locked position even after the locking means have been depressed, said elastic means being mounted within a central opening formed in the casing.

11. A self-locking safety hypodermic syringe holder for use with a syringe having a syringe barrel and a needle assembly, the holder comprising:

an elongated tubular casing, said casing having a central opening extending therethrough defined by an inner annular wall, said annular wall being formed with a pair of diametrically opposite elongated grooves extending in parallel relationship to a longitudinal axis of the casing, a plurality of inwardly extending ridges formed at a proximal end of the casing to provide a stop for a forward end of the syringe barrel when the hypodermic syringe is assembled with the holder, a distal end of the casing being provided with an enlarged flange plate, said flange plate having a groove for receiving a flange plate of the syringe barrel in a locking engagement therein; and an elongated hollow needle guard telescopically coaxially engaged with the casing, said needle guard being movable between a locked position substantially covering the needle assembly and a selectively variable plurality of retracted positions allowing at least a portion of the needle to extend from the needle guard, said needle guard being provided with means for preventing misalignment of the needle guard in relation to the casing.

12. The device of claim 11, wherein said means for preventing misalignment, comprise a pair of diametrically opposite pair of outwardly extending projections slidably receivable within corresponding grooves formed in an end plate which restricts a central opening of the casing in its proximal end.

13. The device of claim 11, wherein a resilient compressible spring means is mounted within the casing in a substantially surrounding relationship to the syringe barrel when the syringe is assembled with the holder.

14. The device of claim 13, wherein said spring means continuously urges the needle guard into a fully extended position, even after the locking tabs have been depressed.

15. The device of claim 14, wherein a plurality of inwardly extending elongated projections are formed in an interior wall of the needle guard, said projections forming an abutting surface at one end of the compressible spring means.

16. The device of claim 11, wherein said casing is provided with a pair of annular ribs formed on an exterior surface of the casing adjacent a proximal end thereof, so as to facilitate manual engagement of the holder device by a user.

* * * * *